United States Patent [19]

DeCamp et al.

[11] Patent Number: 5,650,523
[45] Date of Patent: Jul. 22, 1997

[54] PROCESS FOR THE DESILYLATION OF A 4-SILYLOXY-TETRAHYDRO-PYRAN-2-ONE

[75] Inventors: Ann E. DeCamp, Plainfield; Alan T. Kawaguchi, Berkeley Heights; Ralph P. Volante, East Windsor, all of N.J.

[73] Assignee: Merck & Co., Inc., Rahway, N.J.

[21] Appl. No.: 696,449

[22] Filed: May 6, 1991

Related U.S. Application Data

[63] Continuation of Ser. No. 484,332, Feb. 26, 1990, abandoned.
[51] Int. Cl.$^6$ .................................................. C07D 309/30
[52] U.S. Cl. .................................................. 549/292
[58] Field of Search .................................................. 549/292

[56] References Cited

U.S. PATENT DOCUMENTS

| 4,224,336 | 9/1980 | Christensen et al. | 514/210 |
| 4,733,003 | 3/1988 | Ide et al. | 549/292 |
| 4,902,811 | 2/1990 | Mori et al. | 549/359 |

OTHER PUBLICATIONS

Green, T.W., "Protective Group in Organic Synthesis", p. 39–50, 1981, John Wiley & Sons, New York.

Primary Examiner—Ba Kim Trinh
Attorney, Agent, or Firm—Carol S. Quagliato; Melvin Winokur

[57] ABSTRACT

A process is described for the removal of a silyl protecting group from the 4-hydroxy group of a tetrahydro-pyran-2-one moiety.

8 Claims, No Drawings

PROCESS FOR THE DESILYLATION OF A 4-SILYLOXY-TETRAHYDRO-PYRAN-2-ONE

This is a continuation of application Ser. No. 484,332, filed Feb. 26, 1990, now abandoned.

BACKGROUND OF THE INVENTION

Hypercholesterolemia is known to be one of the prime risk factors for ischemic cardiovascular disease, such as arteriosclerosis. Bile acid sequestrants have been used to treat this condition; they seem to be moderately effective but they must be consumed in large quantities, i.e. several grams at a time, and they are not very palatable.

MEVACOR® (lovastatin), now commercially available is one of a group of very active antihypercholesterolemic agents that function by limiting cholesterol biosynthesis by inhibiting the enzyme, HMG-CoA reductase. In addition to the natural fermentation products, mevastatin and lovastatin, there are a variety of semi-synthetic and totally synthetic analogs thereof.

The preparation of the semi-synthetic and totally synthetic analogs generally involves silyl group protection of the 4-hydroxy group on these mevalonic acid derivatives. The silyl protecting group must eventually be removed, typically in the last step of the synthetic route. In prior efforts, the desilylation has been accomplished with tetra-n-butylammonium fluoride or dilute HF or methanesulfonic acid. The fluoride-based desilylation procedures were problematic on a large scale due to the corrosive properties of the reagent on pilot plant equipment. The methanesulfonic acid desilylation procedure was undesirable because it caused opening of the lactone moiety, which necessitated the introduction of a relactonization step.

The present invention introduces a novel desilylation procedure which has the advantage of increased yield over the prior procedures and increased ease of operation. The process of the present invention is not corrosive to pilot plant equipment and does not cause reactions at the lactone carbonyl.

DETAILED DESCRIPTION OF THE INVENTION

The present invention is a process for the removal of a silyl protecting group from the 4-hydroxy group of a tetrahydro-pyran-2-one moiety.

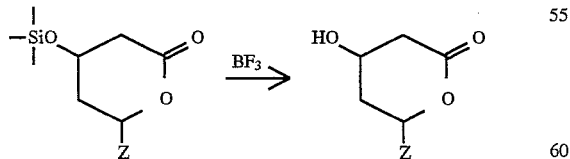

wherein Z represents a lipophilic group such as a polyhydronaphthyl moiety or an aryl or heteroaryl moiety. More particularly the present invention, in its application to the preparation of HMG-CoA reductase inhibitors, is a process for the desilylation of a compound (I):

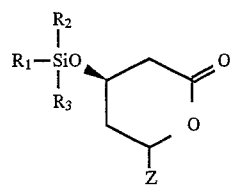

wherein $R_1$, $R_2$, and $R_3$ are each independently selected from:

a) $C_1$–$C_4$alkyl;

b) phenyl;

c) phenyl-$CH_2$—;

d) p-$CH_3$-phenyl$CH_2$; and

Z is selected from:

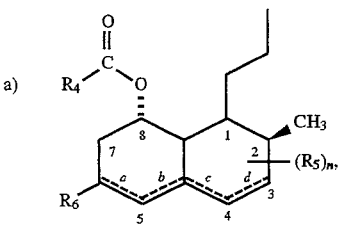

wherein:

$R_4$ is $C_1$–$C_{10}$alkyl;

$R_5$ is selected from:
 a) $C_1$–$C_3$alkyl;
 b) hydroxy;
 c) oxo;
 d) $C_1$–$C_3$alkyl substituted with hydroxy;

n is 0, 1 or 2;

$R_6$ is selected from:
 a) hydrogen;
 b) $C_1$–$C_3$alkyl;
 c) $C_1$–$C_3$alkyl substituted with hydroxy; or
 d) hydroxy; and a, b, c, and d are all single bonds or a and c are double bonds or b and d are double bonds or one of a, b, c, d is a double bond;

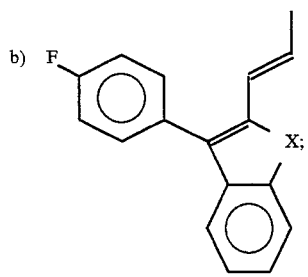

wherein X is NCH(CH$_3$)$_2$ or C(CH$_2$)$_4$

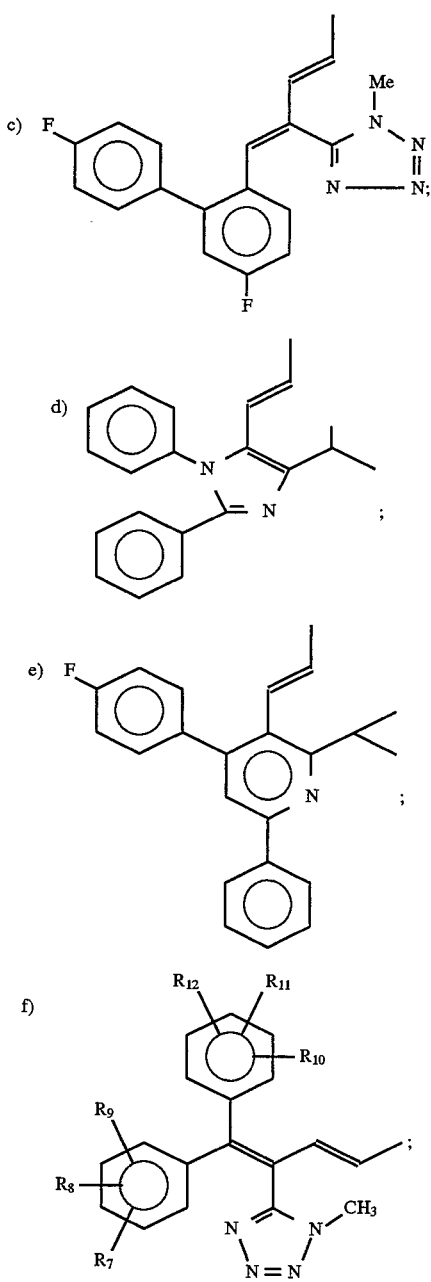

wherein R$_7$ and R$_{10}$ are each independently selected from hydrogen, halogen, C$_{1-4}$alkyl, C$_{1-4}$ alkoxy or trifluoromethyl;

R$_8$, R$_9$, R$_{11}$ R$_{12}$ are each independently selected from Hydrogen, halogen, C$_{1-4}$alkyl, or C$_{1-4}$alkoxy;

which comprises:

contacting of a compound of formula (I) in a polar aprotic solvent such as acetonitrile, dichloromethane, tetrahydrofuran, ethyl acetate, or a mixture thereof; with boron trifluoride etherate, at a temperature of about −10° to 24° C. for about 15 minutes to one hour, to yield a compound of formula (II):

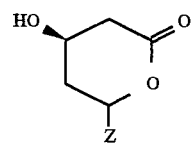

The preferred silyloxy protecting groups are trimethylsilyloxy, triethylsilyloxy, isopropyldimethylsilyloxy, t-butyldimethylsilyloxy, (triphenylmethyl)-dimethylsilyloxy, t-butyldiphenylsilyloxy, methyldiisopropylsilyloxy, tribenzylsilyloxy, tri-p-xylylsilyloxy, triisopropylsilyloxy and triphenylsilyloxy. Most preferred are t-butyldimethysilyloxy and trimethylsilyloxy.

The moiety Z may be any lipophilic group which is compatable with the boron trifluoride reactant. Preferably Z is selected from:

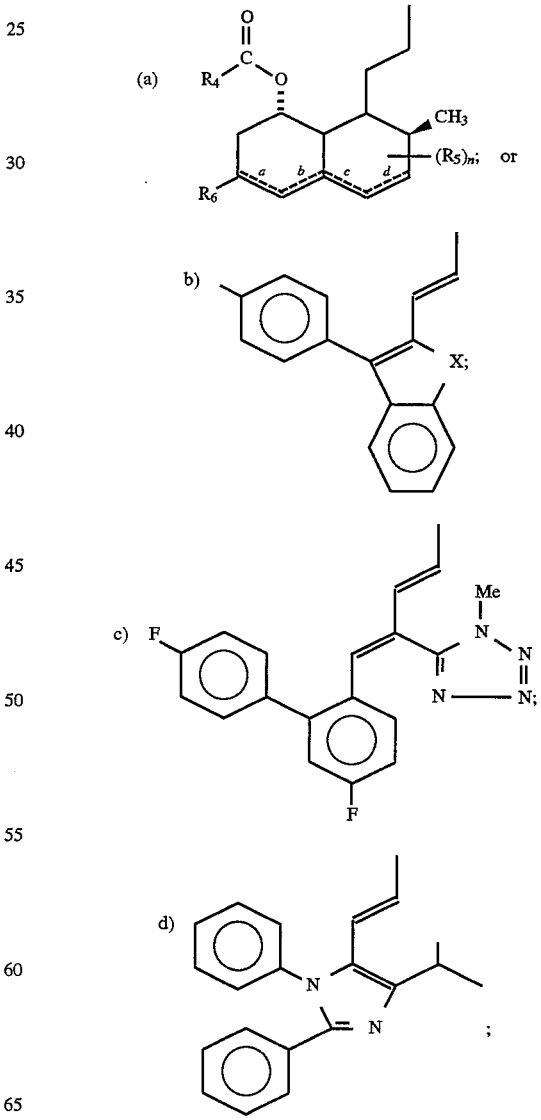

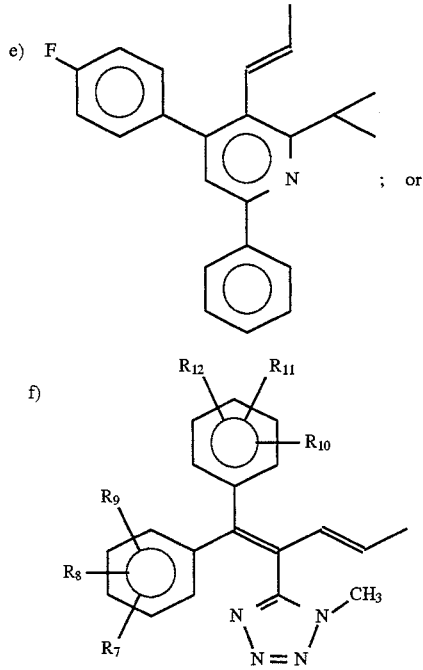

e)

f)

A preferred use of the present invention is the preparation of compounds (II) wherein Z is the polyhydronaphthyl group (a) and $R_4$ is 2-butyl or 2,2-dimethylpropyl, and $R_6$ is hydrogen, methyl, hydroxy or hydroxymethyl and n is 0 or 1, wherein, when n is 1, $R_5$ is hydroxy in the 5-position or oxo in the 3-position or (1-hydroxyethyl) in the 7-position, and b and d are double bonds or a and c are double bonds or a b c d are single bonds provided that when $R_6$ is hydroxy, b and d are double bonds and when $R_5$ is 3-oxo a and c are double bonds, and, when $R_5$ is hydroxy, a, b, c and d are all single bonds.

The most preferred use is in the preparation of Compounds (II) wherein (a) $R_4$ is 2,2-dimethylpropyl, $R_6$ is $CH_3$, n is 0 and b and d are double bonds;

(b) $R_4$ is 2,2-dimethylpropyl, $R_6$ is $CH_3$, n is 1, $R_5$ is 5—OH, a, b, c, d are all single bonds;

(c) $R_4$ is 2,2-dimethylpropyl, $R_6$ is $CH_3$, n is 1, $R_5$ is 3-oxo, a and c are double bonds;

(d) $R_4$ is 2,2-dimethylpropyl, $R_6$ is $CH_3$, n is 1, $R_5$ is (1-hydroxyethyl) in the 7-position, b and d are double bonds;

(e) $R_4$ is 2-butyl, $R_6$ is $CH_3$, n is 0 and b and d are double bonds;

(f) $R_4$ is 2,2-dimethylpropyl, $R_6$ is $CH_2OH$, n is 0 and b and and d are double bonds.

The present invention comprises desilylation at the 4-hydroxy group of a tetrahydro-pyran-2-one moiety. Specifically the process comprises the treatment of a compound (I) with boron trifluoride in a polar aprotic solvent such as $CH_3CN$, THF, $CH_2Cl_2$, EtoAc, or a mixture thereof, at a temperature of about −10° to +25° C.

The preferred solvent is $CH_3CN$ at a temperature of about 0° to 5° C. Approximately equivalent amounts of (I) to $BF_3$ are treated together. After treatment with $BF_3$ the reaction mixture is quenched with aqueous $NaHCO_3$, the phases, separated and the organic layer washed with aqueous NaCl, concentrated, distilled, and finally allowed to crystallize to product (II).

Hydroxyl groups contained in compounds of formula (I) may be silylated according to the procedures in U.S. Pat. No. 4,444,784.

Compounds of formula (I) may contain, in the Z moiety, a hydroxyl group which may be protected as a silyloxy group. In this case the mole ratio of $BF_3$ to compound (I) can be increased so that all silyloxy protecting groups are removed in one step. It should be understood that, where $R_5$ or $R_6$ substituent groups contain hydroxy, protected hydroxy such as silyloxy are also included on compounds of formula (I) within the present invention.

EXAMPLE 1

Preparation of 6(R)-[2-[8(S)-(2,2-dimethylbutyryloxy)-2 (S),6(R)-dimethyl-5(R)-hydroxy-,1,2,3,4,4a(R),5,6,7,8,8a (R)-decahydronaphthyl-1(S)]ethyl]-4(R)-hydroxy-3,4,5,6,-tetrahydro-2H-pyran-2-one.

A dry two liter, three neck flask equipped with an overhead stirrer, a nitrogen inlet, a temperature probe, and a septum was charged with 6(R)-[2-[8(S)-(2,2-dimethylbutyryloxy)-2(S),6(R)-dimethyl-5(R)-hydroxy-,1, 2,3,4,4a(R),5,6,7,8,8a(R)-decahydronaphthyl-1(S)]ethyl]-4 (R)-tert-butyldimethylsilyloxy-3,4,5,6,-tetrahydro-2H-pyran-2-one, (50.0 g, 0.0904 mole) and acetonitrile (500 mL). The clear colorless solution was cooled to 0°–3° C. Boron trifluoride etherate (12.5 mL, 0.102 mole,) was added by syringe over 2.0 min, and the resulting pale yellow solution was stirred at 0°–3° C. until the reaction was complete (about 30 min).

The reaction was quenched by the addition of $NaHCO_3$ solution (41.4 mg/mL, aqueous, 300 mL,) over 5–7 min while keeping the temperature ≦10° C. The mixture was then vigorously stirred for 1.0 h while being allowed to warm to 20° C. The phases were separated, and the pale yellow organic phase washed with NaCl solution (saturated, aqueous, 300 mL). The organic layer was concentrated in vacuo to one half volume (internal temp. ≦30° C.), then switched over to isopropyl acetate by dilution with isopropyl acetate followed by distillation to a final volume of 1250 mL. The solution was washed with deionized water (750 mL) and then transferred to a two liter, three neck flask equipped with an overhead stirrer and a distillation apparatus. The residual water was removed by azeotropic vacuum distillation with isopropyl acetate (500 mL, internal temp. ≦30° C.) to a KF ≦500 μg/mL. The volume was adjusted to 280 mL, and the solution was seeded, if necessary. The product was allowed to crystallize at 25° C. for 30 min. Hexanes (840 mL) were then added slowly over 1.0 h. The mixture was aged at 25° C. for 30 min and then at −5° C. overnight (17 h). The product was collected by filtration on a sintered glass funnel, and the crystals washed with cold (−10° C.) isopropyl acetate in hexanes 25 v/v % (2×30 mL). The white crystalline solids were dried in vacuo at 25° C. with a nitrogen sweep to give the title compound in a yield of 87%.

EXAMPLES 2–5

Employing the procedure substantially as described in Example 1, but substituting for the silylated alcohol therein an approximately equimolar amount of the compounds (I) described in table I there are prepared the desilylated products (II) also described in table I.

TABLE I

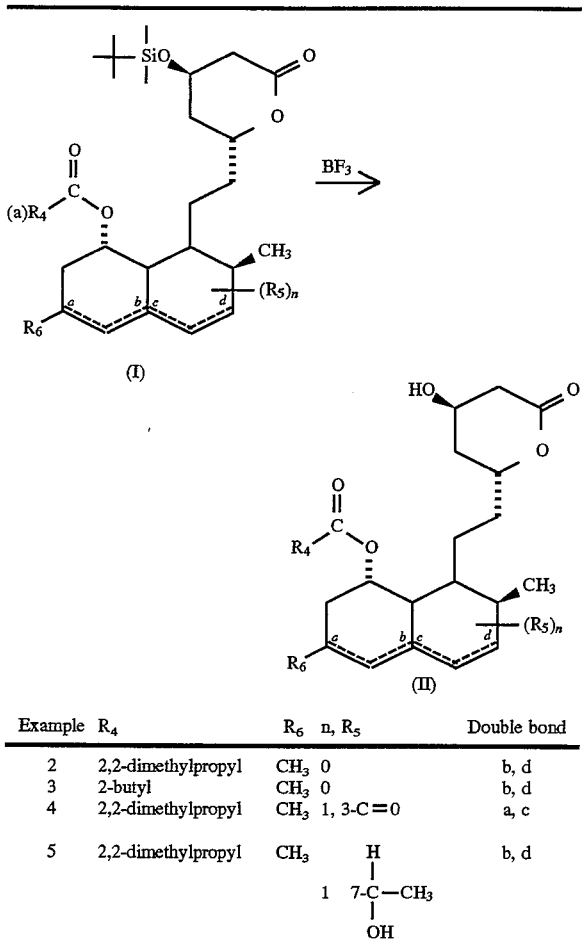

| Example | R₄ | R₆ | n, R₅ | Double bond |
|---------|-----|-----|-------|-------------|
| 2 | 2,2-dimethylpropyl | CH₃ | 0 | b, d |
| 3 | 2-butyl | CH₃ | 0 | b, d |
| 4 | 2,2-dimethylpropyl | CH₃ | 1, 3-C=O | a, c |
| 5 | 2,2-dimethylpropyl | CH₃ | 1  7-C—CH₃<br>          \|<br>          OH | b, d |

What is claimed is:

1. A process for the desilylation of a compound (I)

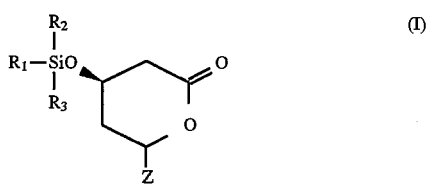

wherein $R_1$, $R_2$, and $R_3$ are each independently selected from:
   a) $C_1$–$C_4$alkyl,
   b) phenyl,
   c) pheny-$CH_2$—, and
   d) p-$CH_3$-phenyl-$CH_2$;

Z is

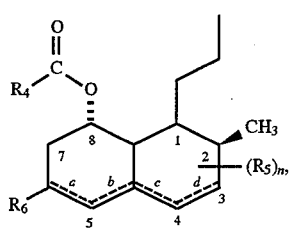

wherein:
   $R_4$ is $C_1$–$C_{10}$alkyl;
   $R_5$ is selected from:
      a) $C_1$–$C_3$alkyl,
      b) hydroxy,
      c) oxo, and
      d) $C_1$–$C_3$alkyl substituted with hydroxy;
   n is 0, 1 or 2;
   $R_6$ is selected from:
      a) hydrogen,
      b) $C_1$–$C_3$alkyl,
      c) $C_1$–$C_3$ alkyl substituted with hydroxy, and
      d) hydroxy; and
   a, b, c, and d are all single bonds or a and c are double bonds or b and d are double bonds or one of a, b, c, d is a double bond;

which comprises:
   contacting a compound of formula (I) in a solvent selected from acetonitrile, $CH_2Cl_2$, THF, ethyl acetate or a mixture thereof, with boron trifluoride etherate at a temperature of about –10° to 24° C. to yield a compound of formula (II):

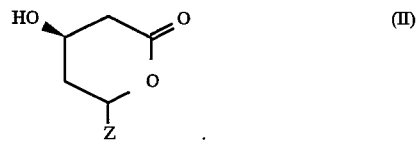

2. The process of claim 1 wherein the silyloxy protecting group is selected from: trimethylsilyloxy, triethylsilyloxy, isopropyldimethylsilyloxy, t-butyldimethylsilyloxy, (triphenylmethyl)-dimethylsilyloxy, t-butyldiphenylsilyloxy, methyldiisopropylsilyloxy, tribenzylsilyloxy, tri-p-xylylsilyloxy, triisopropylsilyloxy or triphenylsilyloxy.

3. The process of claim 2 wherein the silyloxy protecting group is tert-butyldimethylsilyoxy or trimethylsilyloxy.

4. A process according to claim 1 wherein: $R_4$ is 2-butyl or 2,2-dimethylpropyl and $R_6$ is H, methyl, hydroxy or hydroxymethyl.

5. A process according to claim 4 where n is 0 or 1.

6. A process according to claim 5 wherein the solvent is acetonitrile.

7. A process according to claim 6 wherein n is 1; and
   a) $R_5$ is 5—OH, a, b, c and d are single bonds;
   b) $R_5$ is 3-oxo, a and c are double bonds or c is a double bond; or
   c) $R_5$ is 7-(1-hydroxyethyl), b and d are double bonds;
provided that when $R_6$ is OH, b and d are double bonds or c is a double bond or a, b, c and d are single bonds.

8. The process according to claim 6 wherein the Compound (II) prepared is selected from:
   a) $R_4$ is 2,2-dimethylpropyl, $R_6$ is $CH_3$, n is 0 and b and d are double bonds;
   b) $R_4$ is 2,2-dimethylpropyl, $R_6$ is $CH_3$, n is 1, $R_5$ is 5—OH, a, b, c and d are all single bonds;
   c) $R_4$ is 2,2-dimethylpropyl, $R_6$ is $CH_3$, n is 1, $R_5$ is 3-oxo and a and c are double bonds;
   d) $R_4$ is 2,2-dimethylpropyl, $R_6$ is $CH_3$, n is 1, $R_5$ is 7-(1-hydroxyethyl) and b and d are double bonds;
   e) $R_4$ is 2,2-dimethylpropyl, $R_6$ is $CH_2OH$, n is 0, and b and d are double bonds;
   f) $R_4$ is 2-butyl, $R_6$ is $CH_3$, n is 0 and b and d are double bonds.

* * * * *